US011227414B2

United States Patent
Dhanantwari et al.

(10) Patent No.: US 11,227,414 B2
(45) Date of Patent: Jan. 18, 2022

(54) RECONSTRUCTED IMAGE DATA VISUALIZATION

(71) Applicant: KONINKLIJKE PHILIPS N.V., Eindhoven (NL)

(72) Inventors: Amar Dhanantwari, Solon, OH (US); Mukta Joshi, Andover, MA (US); Yael Nae, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/782,690

(22) PCT Filed: Mar. 28, 2014

(86) PCT No.: PCT/IB2014/060253
§ 371 (c)(1),
(2) Date: Oct. 6, 2015

(87) PCT Pub. No.: WO2014/167450
PCT Pub. Date: Oct. 16, 2014

(65) Prior Publication Data
US 2016/0048982 A1 Feb. 18, 2016

Related U.S. Application Data

(60) Provisional application No. 61/810,353, filed on Apr. 10, 2013.

(51) Int. Cl.
*G06T 11/00* (2006.01)
*G06T 5/00* (2006.01)
(Continued)

(52) U.S. Cl.
CPC ............ *G06T 11/003* (2013.01); *A61B 6/032* (2013.01); *A61B 6/461* (2013.01); *A61B 6/467* (2013.01);
(Continued)

(58) Field of Classification Search
None
See application file for complete search history.

(56) References Cited

U.S. PATENT DOCUMENTS 6,623,431 B1 9/2003 Sakuma
7,088,849 B1 8/2006 Toth
(Continued)

FOREIGN PATENT DOCUMENTS

DE 102008052691 A1 4/2010
EP 0981998 A1 3/2000
(Continued)

OTHER PUBLICATIONS

Sakellaropoulos, P., et al.; An image visualization tool in mammography; 1999; Med. Inform.; 24(1)53-73.

*Primary Examiner* — Jiangeng Sun
(74) *Attorney, Agent, or Firm* — Larry Liberchuk

(57) ABSTRACT

A method includes processing projection data with a first reconstruction algorithm and reconstructing first reconstructed volumetric image data, wherein the first reconstructed volumetric image data has a first 3D noise function. The method further includes processing the same projection data with a second different reconstruction algorithm and reconstructing second reconstructed volumetric image data, wherein the second reconstructed volumetric image data has a second 3D noise function, which is different from the first 3D noise function. The method further includes visually presenting the first or the second reconstructed volumetric image data in a main viewport. The method further includes visually presenting a sub-portion the other of the first or the second reconstructed volumetric image data in a region of interest overlaid over a sub-portion of the main viewport.

15 Claims, 4 Drawing Sheets

(51) Int. Cl.
*G06T 7/00* (2017.01)
*G06T 11/60* (2006.01)
*G06T 15/08* (2011.01)
*A61B 6/03* (2006.01)
*A61B 6/00* (2006.01)

(52) U.S. Cl.
CPC ............ *G06T 5/002* (2013.01); *G06T 7/0012* (2013.01); *G06T 11/60* (2013.01); *G06T 15/08* (2013.01); *G06T 2200/04* (2013.01); *G06T 2207/10081* (2013.01); *G06T 2207/30024* (2013.01); *G06T 2210/41* (2013.01); *G06T 2211/421* (2013.01)

(56) References Cited

U.S. PATENT DOCUMENTS

| | | | |
|---|---|---|---|
| 7,756,312 | B2 | 7/2010 | Hsieh et al. |
| 8,077,153 | B2* | 12/2011 | Benko ................... G06F 3/0488 345/173 |
| 8,081,809 | B2 | 12/2011 | Dutta et al. |
| 8,285,364 | B2 | 10/2012 | Barbagli |
| 2007/0014480 | A1 | 1/2007 | Sirohey et al. |
| 2007/0201813 | A1* | 8/2007 | Onoda ................. H04N 9/8205 386/248 |
| 2008/0159643 | A1 | 7/2008 | Huang et al. |
| 2009/0256565 | A1 | 10/2009 | Marinelli et al. |
| 2010/0097378 | A1 | 4/2010 | Barth et al. |
| 2011/0052030 | A1 | 3/2011 | Bruder et al. |
| 2011/0282181 | A1 | 11/2011 | Wang et al. |
| 2011/0286629 | A1 | 11/2011 | Dennerlein |
| 2012/0018645 | A1 | 1/2012 | Vija |
| 2014/0153809 | A1* | 6/2014 | Koehler ................. A61B 6/032 382/131 |

FOREIGN PATENT DOCUMENTS

| | | |
|---|---|---|
| EP | 2385494 A1 | 11/2011 |
| JP | 2003153893 A | 5/2003 |
| RU | 2166909 C1 | 5/2001 |
| RU | 2252692 A | 1/2005 |
| WO | 0007146 A1 | 2/2000 |
| WO | 2007034342 A2 | 3/2007 |
| WO | 2008146186 A2 | 12/2008 |
| WO | 2009083864 A2 | 7/2009 |
| WO | 2009091824 A1 | 7/2009 |
| WO | 2009129137 A1 | 10/2009 |
| WO | 2010082101 A1 | 7/2010 |
| WO | 2011036624 A1 | 3/2011 |
| WO | 2011046425 A2 | 4/2011 |
| WO | 2012131520 A2 | 10/2012 |

* cited by examiner

RECONSTRUCTED IMAGE DATA VISUALIZATION

CROSS REFERENCE TO RELATED APPLICATIONS

This application is a national filing of PCT application Serial No. PCT/IB2014/060253, filed Mar. 28, 2014, published as WO 2014/167450 A1 on Oct. 16, 2014, which claims the benefit of U.S. provisional application Ser. No. 61/810,353 filed Apr. 10, 2013, which is incorporated herein by reference.

The following generally relates to reconstructed image data visualization and is described with particular application to computed tomography (CT). However, the following is also amenable to other modalities.

Radiologists have been trained to read images that have a certain appearance due to noise, which has been used as an indicator of certain properties of the image. For example, the noise may provide a reviewer with a confidence level for structures, shapes and/or contours in the image. By way of example, higher visible noise may indicate a lower probability that the visualized structures, shapes and contours represent the true structures, shapes and contours, and lower visible noise may indicate a higher probability that the visualized structures, shapes and contours represent the true structures, shapes and contours.

In another example, the texture of the image provides an indication of the underlying spatial resolution of the image. By way of example, blotchy noise may indicate lower resolution, and fine noise may indicate higher resolution. In another example, the appearance of noise in a sub-portion of a region of tissue visualized with a same gray scale range may indicate that the region includes different tissues. By way of example, the range may be just within the noise of one tissue, resulting in some gray pixels, and outside the noise of another tissue allowing the reviewer to discriminate between the two tissues without needing to shift the gray scale range.

De-noising algorithms (projection and/or image domain) and advanced reconstruction techniques have been used to reduce noise in the reconstructed image data. However, the reduction of noise also removes (in part or in full, dependent on the de-noising algorithm) the visual clues discussed above that image reviewers use to determine the confidence level and/or the resolution, and/or distinguish different tissue. Unfortunately, this may lead to a reluctance of a radiologist to employ a de-noising reconstruction algorithm since the resulting reconstructed images may have different characteristics compared to images they have been trained to review.

Aspects described herein address the above-referenced problems and others.

The following describes an approach in which reconstructed image data, reduced noise (or de-noised) reconstructed image, and/or a combination thereof is concurrently visually presented to an observer, which allows for visually presenting and/or observing the visual clues noise provides and/or observing noise reduced (default or user defined) image data, which may better show features of interest that could otherwise be obscured by the removed noise.

In one aspect, a method includes processing projection data with a first reconstruction algorithm and reconstructing first reconstructed volumetric image data, wherein the first reconstructed volumetric image data has a first 3D noise function. The method further includes processing the same projection data with a second different reconstruction algorithm and reconstructing second reconstructed volumetric image data, wherein the second reconstructed volumetric image data has a second 3D noise function, which is different from the first 3D noise function. The method further includes visually presenting the first or the second reconstructed volumetric image data in a main viewport. The method further includes visually presenting a sub-portion the other of the first or the second reconstructed volumetric image data in a region of interest overlaid over a sub-portion of the main viewport.

In another aspect, a method includes processing projection data with a first reconstruction algorithm and reconstructing first reconstructed volumetric image data, wherein the first reconstructed volumetric image data has a first 3D noise function. The method further includes processing the same projection data with a second different reconstruction algorithm and reconstructing second reconstructed volumetric image data, wherein the second reconstructed volumetric image data has a second 3D noise function, which is different from the first noise function. The method further includes obtaining a noise level of interest. The method further includes combining the first and second volumetric imaged data, creating combined volumetric image data, based on the noise level of interest. The method further includes visually displaying the combined volumetric image data.

In another aspect, a system includes a reconstruction apparatus that reconstructs a same set of projection data with different reconstruction algorithms, generating first and second reconstructed image data. One of the reconstruction algorithms is a de-noising reconstruction algorithm. The reconstruction apparatus, at least one of: visually displays the first or second reconstructed image data with an overlay including a sub-portion of the de-noised reconstructed image data and superimposed over a sub-portion of the visually displayed image data, or combines the first and the second reconstructed image data based on an input noise level, creating combined image data, and visually displays the combined image data.

The invention may take form in various components and arrangements of components, and in various steps and arrangements of steps. The drawings are only for purposes of illustrating the preferred embodiments and are not to be construed as limiting the invention.

FIG. 1 schematically illustrates an imaging system including a reconstruction apparatus.

The following describes an approach in which non, reduced noise reconstructed image data, reduced noise (or de-noised) reconstructed image, and/or a combination thereof is visually presented to an observer, which allows for visually presenting and/or observing the visual clues noise provides and/or observing noise reduced (default or user defined) image data, which may better show features of interest that could otherwise be obscured by the removed noise.

Figure 1:
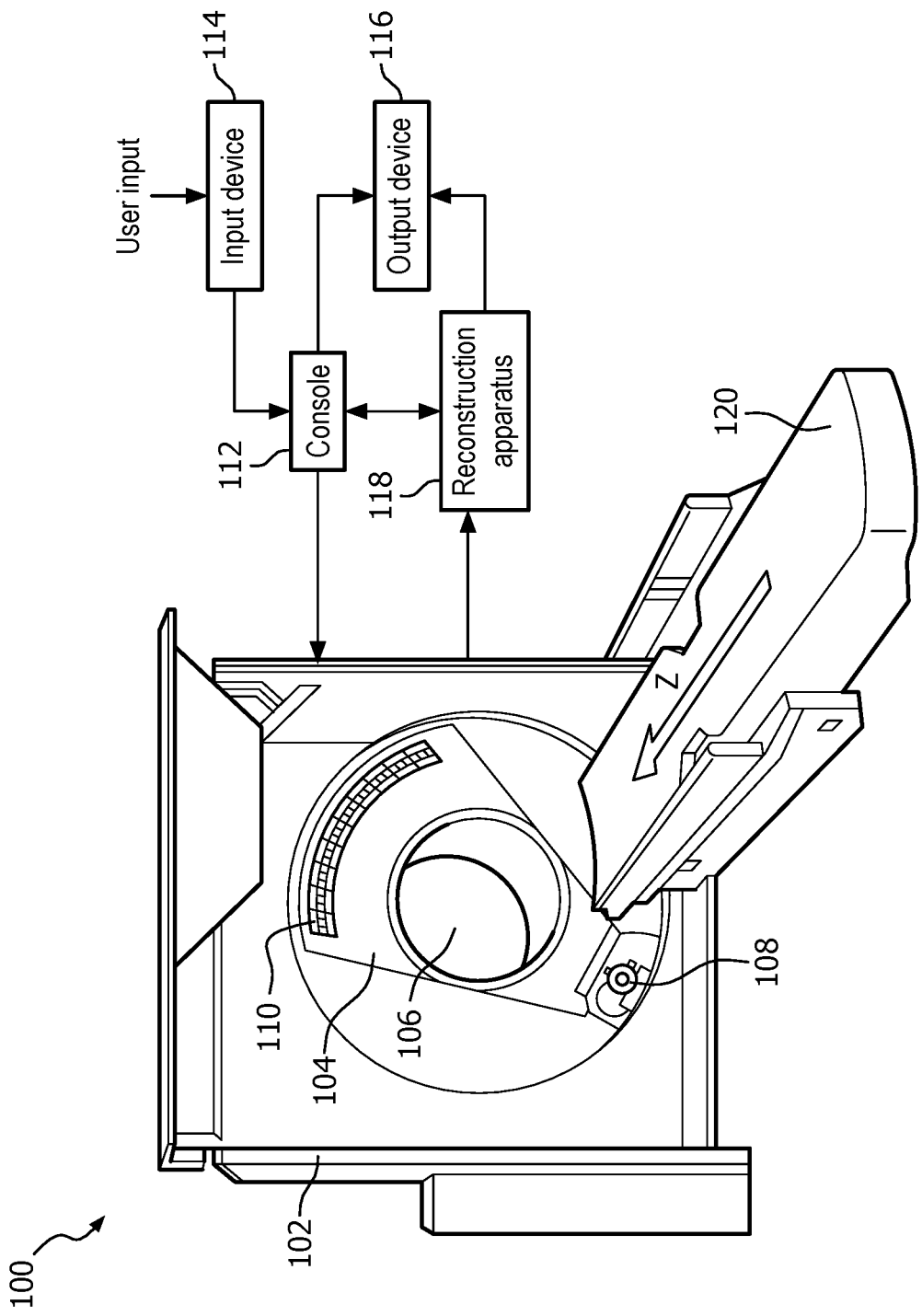

FIG. 1 illustrates an imaging system 100 such as a computed tomography (CT) scanner.

The imaging system 100 includes a generally stationary gantry 102 and a rotating gantry 104. The rotating gantry 104 is rotatably supported by the stationary gantry 102 and rotates around an examination region about a longitudinal or z-axis.

A patient support 120, such as a couch, supports an object or subject such as a human patient in the examination region. The support 120 is configured to move the object or subject for loading, scanning, and/or unloading the object or subject.

A radiation source 108, such as an x-ray tube, is rotatably supported by the rotating gantry 104. The radiation source 108 rotates with the rotating gantry 104 and emits radiation that traverses the examination region 106.

A radiation sensitive detector array 110 subtends an angular arc opposite the radiation source 108 across the examination region 106. The detector array 110 includes one or more rows of detectors that extend along the z-axis direction, detects radiation traversing the examination region 106, and generates projection data indicative thereof.

A general-purpose computing system or computer serves as an operator console 112 and includes an input device(s) 114 such as a mouse, a keyboard, and/or the like and an output device(s) 116 such as a display monitor, a filmer or the like. The console 112 allows an operator to control operation of the system 100. This includes selecting one or more reconstruction algorithms, such as a filtered-backprojection, a reduced noise, a combination thereof and/or other reconstruction algorithm, activating and positioning a moveable region of interest (ROI) overlay over a sub-portion of a first reconstruction to display second different reconstructed image data in the ROI and/or a viewport associated therewith, indicating a noise level for a reconstruction, etc.

A reconstruction apparatus 118 processes the projection data and reconstructs volumetric image data. As described in greater detail below, in one instance, the reconstruction apparatus 118 produces non, reduce noise reconstructed volumetric image data, reduced noise (or de-noised) reconstructed volumetric image, and/or a combination thereof. The resulting volumetric image data can be visually presented, allowing for visualizing the clues noise provides in volumetric image data. The reduced noise and/or combined reconstructed volumetric image data can be concurrently and/or individually displayed. This data may better show features of interest that would otherwise be obscured by the removed noise. The data can be displayed through one or more display monitors of the output device(s) 116.

As further described in greater detail below, the reconstruction apparatus 118 may employ a filtered-backprojection (FBP) reconstruction, a (image domain and/or projection domain) reduced noise reconstruction algorithm (e.g., an iterative reconstruction) and/or other algorithm. It is to be appreciated that the reconstruction apparatus 118 can be implemented through a microprocessor(s), which executes a computer readable instruction(s) encoded or embed on computer readable storage medium such as physical memory and other non-transitory medium. Additionally or alternatively, the microprocessor(s) can execute a computer readable instruction(s) carried by a carrier wave, a signal and other transitory (or non, non-transitory) medium.

Figure 2:
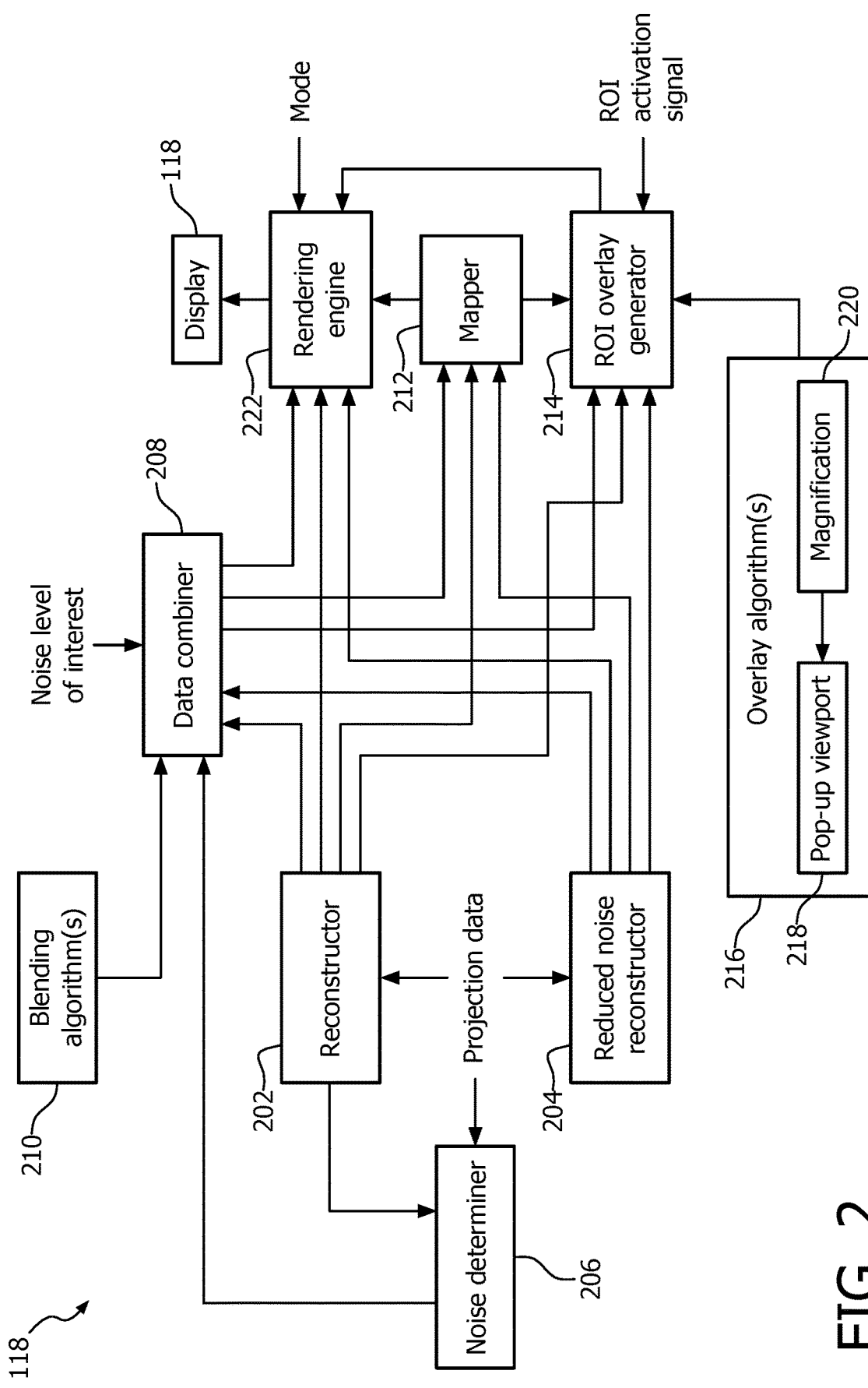
FIG. 2 illustrates a non-limiting example of the reconstruction apparatus of FIG. 1.

FIG. 2 schematically illustrates an example of the reconstruction apparatus 118.

A reconstructor 202 processes projection data, which may be generated by the imaging system 100 and/or other imaging system, and can be obtained from the imaging system and/or a data repository such as a picture archiving and communication system (PACS), a radiology information system (RIS), a hospital information system (HIS), and/or other data repository. The illustrated reconstructor 202 employs a filtered-backprojection, cone-beam and/or other non, noise-reducing reconstruction algorithm. The reconstructor 202 processes the projection data and generates reconstructed volumetric image data.

A reduced noise reconstructor 204 processes the same projection data. However, the reconstructor 202 employs a noise reducing reconstruction algorithm, which may include an iterative and/or other noise reducing reconstruction algorithm. The reduced noise reconstructor 202 generates reduced noise (or de-noised) reconstructed volumetric image data, which has a noise level (e.g., standard deviation across the entire image or a sub-portion thereof) that is less than a noise level of a corresponding region of the reconstructed volumetric image data generated by the reconstructor 202.

In the illustrated embodiment, the reconstructor 202 and the reduced noise reconstructor 204 are shown as two different reconstructors. However, in a variation, the reconstructor 202 and the reduced noise reconstructor 204 are the same reconstructor, reconstructing the same projection data using two different reconstruction algorithms, and generating two different sets of reconstructed image data, non, reduced noise reconstructed image data and reduced noise reconstructed image data.

A noise determiner 206 determines a noise (e.g., 3D function, mean, etc.) for the reconstructed volumetric image data and/or a sub-portion thereof, and/or the reduced noise reconstructed volumetric image data and/or a sub-portion thereof. In the illustrated embodiment, the noise determiner 206 may additionally or alternatively determine the noise based on the projection data. Additionally or alternatively the noise estimates can be based on a difference between the reconstructed volumetric image data and the reduced noise reconstructed volumetric image data. Other approaches are also contemplated herein.

A data combiner 208 combines the non, reduced noise reconstructed volumetric image data and the reduced noise reconstructed volumetric image data, producing combined volumetric image data. In the illustrated embodiment, the data combiner 208 combines the non, reduced noise reconstructed volumetric image data and the reduced noise reconstructed volumetric image data based on a blending algorithm(s) 210, the noise value of each of the non, reduced noise reconstructed volumetric image voxel and the reduced noise reconstructed volumetric image voxel and a target noise level. The target noise level may be based on a default and/or user defined (e.g., as determined by an input noise level of interest signal indicative of noise level (e.g., standard deviation, variance, etc.) of interest).

A mapper 212 creates a physical mapping or map between voxels of the non, reduced noise reconstructed volumetric image data, the reduced noise reconstructed volumetric image data, and/or the combined volumetric image data. For example, the map maps each voxel (x,y,z) of each of the non, reduced noise reconstructed volumetric image data, the reduced noise reconstructed volumetric image data, and/or the combined volumetric image data to a voxel of the other of the non, reduced noise reconstructed volumetric image data, the reduced noise reconstructed volumetric image data, and/or the combined volumetric image data.

A region of interest (ROI) overlay generator 214, when activated, generates a ROI overlay, which is overlaid over and can be moved about rendered volumetric image data, based on an overly algorithm(s) 216. Activation can be in response to receiving a ROI activation input signal, indicative of a user actuating a control (e.g., a physical button, a mouse click, touch of an area of a touch screen, voice recognition, etc.) which invokes activation. The mouse click and/or touch area may be in the form of a button, a dial, a slider, a drop down menu, etc. Without activation or upon termination of activation, the region of interest (ROI) overlay generator 214 removes any overlaid ROI overlay from display. Termination can be invoked through the user actuating the same and/or other control.

Generally, the ROI overlay, when overlaid or superimposed over first displayed reconstructed volumetric image data, identifies a region of the rendered first displayed volumetric image data where second volumetric image data that was reconstructed with a second different reconstruction algorithm is visually presented. The second volumetric image data visually presented in the ROI overlay corresponds to a same location within the first displayed reconstructed volumetric image data as the first displayed reconstructed volumetric image data behind the ROI overlay. The map of the mapper 212 provides this mapping. The ROI overlay can be selected from a set of pre-determined shapes (e.g., circular, elliptical, rectangular, irregular, etc.), drawn free hand by a user, and/or otherwise created. Additionally, a ROI overlay can be re-sized, re-shaped, and/or otherwise manipulated.

Optionally, a pop up viewport 218 can be displayed, over a portion of the first displayed reconstructed volumetric image data and/or in an area not overlaying the first displayed reconstructed volumetric image data. The viewport 218 can be similarly activated and/or terminated. The viewport 218, generally, has a larger viewing area relative to the ROI overlay and displays that same information when a magnification 220 corresponds to a difference between or ratio of the ROI overlay and viewport viewing areas geometry. Increasing the magnification 220 may increase the viewport viewing area accordingly and/or zoom in and not show regions at the outer perimeter. Where the viewport 218 is activated, the ROI overlay may visually present the first reconstructed volumetric image data (like the area outside of the ROI overlay) or the second reconstructed volumetric image data (like the viewport 218).

A rendering engine 222 renders data via a display monitor of the output device(s) 116. This includes rendering one or more of the non, reduced noise reconstructed volumetric image data, the reduce noise reconstructed volumetric image data, and/or the combined reconstructed image data. Optionally, the rendering engine 222 renders can render the ROI overlay. Optionally, the rendering engine 222 can render the pop up viewport 218. A input indicative of a mode of operation determines what the rendering engine 222 renders.

Figure 3:
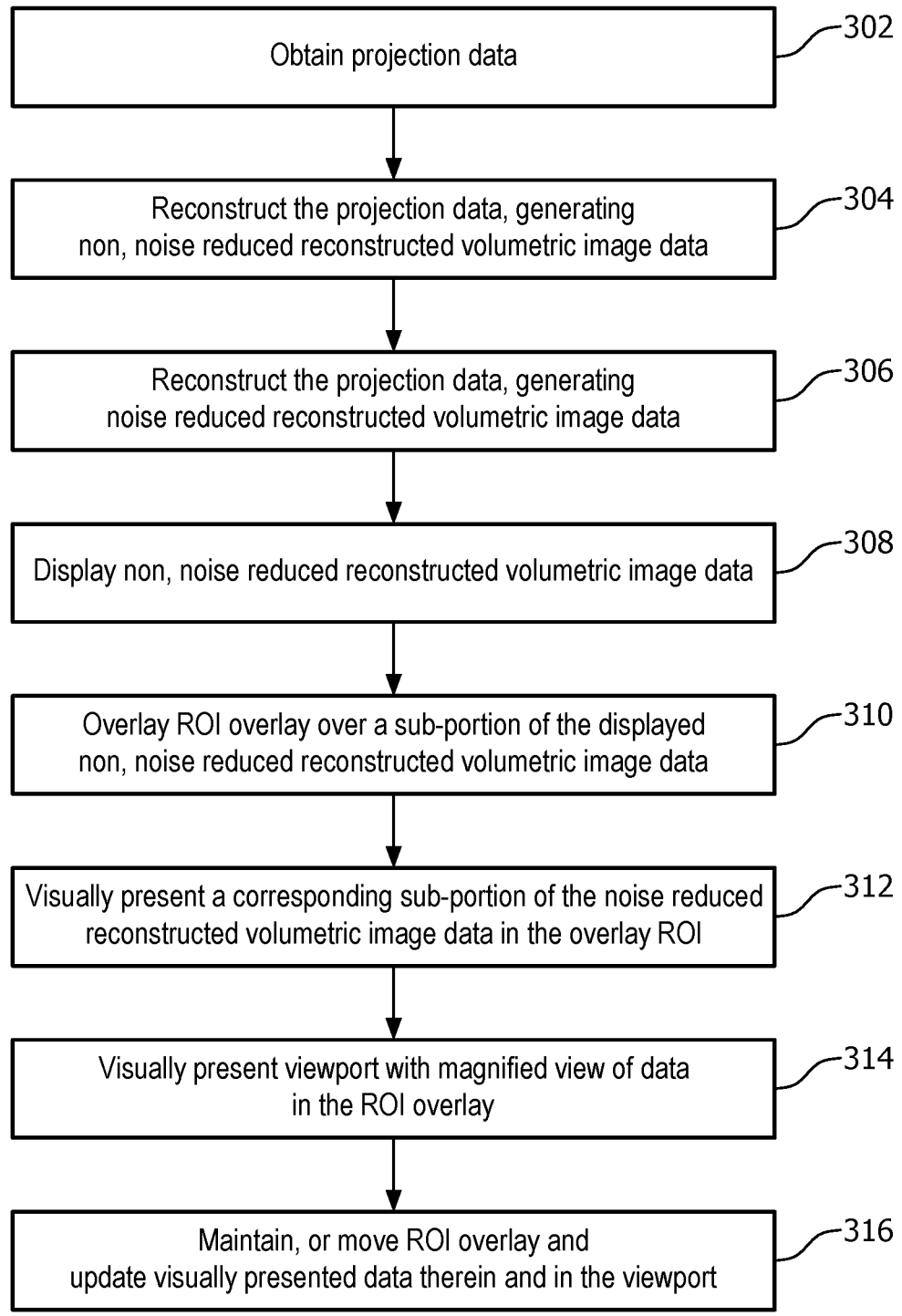
FIG. 3 illustrates an example method for reconstructing the same projection data with two different reconstruction algorithms, one a de-noising reconstruction algorithm, and concurrently displaying the reconstructed image data of both reconstruction algorithms.

FIG. 3 illustrate an example method in which a moveable ROI overlay and optional viewport is overlaid over rendered reconstructed volumetric image data.

It is to be appreciated that the ordering of the acts in the method is not limiting. As such, other orderings are contemplated herein. In addition, one or more acts may be omitted and/or one or more additional acts may be included.

At 302, projection data is obtained.

At 304, a reconstructor reconstructs the projection data, generating non, reduced noise reconstructed volumetric image data.

At 306, the same or different reconstructor reconstructs the projection data, generating reduced noise (or de-noised) reconstructed volumetric image data.

At 308, the non, noise reduced reconstructed volumetric image data is displayed in a main display region.

At 310, an ROI overlay is overlaid over a sub-portion of the displayed non, noise reduced reconstructed volumetric image data.

At 312, a sub-portion of the reduced noise reconstructed volumetric image data corresponding to the non, noise reduced reconstructed volumetric image data is displayed in the ROI overlay.

At 314, where activated, a pop up viewport is also displayed and includes the same data as in the ROI overlay, but magnified.

At 316, the ROI overlay is maintained, or moved where the visually presented data is updated in the ROI overlay and the viewport to reflect the location.

The above acts may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

In a variation of the above, the reduced noise reconstructed volumetric image data is displayed in the display region and the non, reduced noise reconstructed volumetric image data or the combined volumetric imaged data is displayed in the ROI overlay. The reduced noise reconstructed volumetric image data, the non, reduced noise reconstructed volumetric image data or the combined volumetric image data is displayed in the pop up viewport.

In another variation, the non, reduced noise reconstructed volumetric image data is displayed in the display region and the combined volumetric image data is displayed in the ROI overlay. The reduced noise reconstructed volumetric image data, the non, reduced noise reconstructed volumetric image data or the combined volumetric image data is displayed in the pop up viewport.

In yet another variation of the above, the reduced noise reconstructed volumetric image data is displayed in the display region and the combined volumetric image data is displayed in the ROI overlay. The reduced noise reconstructed volumetric image data, the non, reduced noise reconstructed volumetric image data or the combined volumetric image data is displayed in the pop up viewport.

In still another variation, the combined volumetric image data is displayed in the display region and either the non, reduced noise reconstructed volumetric image data or the reduced noise reconstructed volumetric image data is displayed in the ROI overlay. The reduced noise reconstructed volumetric image data, the non, reduced noise reconstructed volumetric image data or the combined volumetric image data is displayed in the pop up viewport.

With any of the above variations, the volumetric image data displayed in the region of interest overlay can be switched between the non, reduced noise reconstructed volumetric image data, the reduced noise reconstructed volumetric image data, or the combined volumetric image data.

Figure 4:
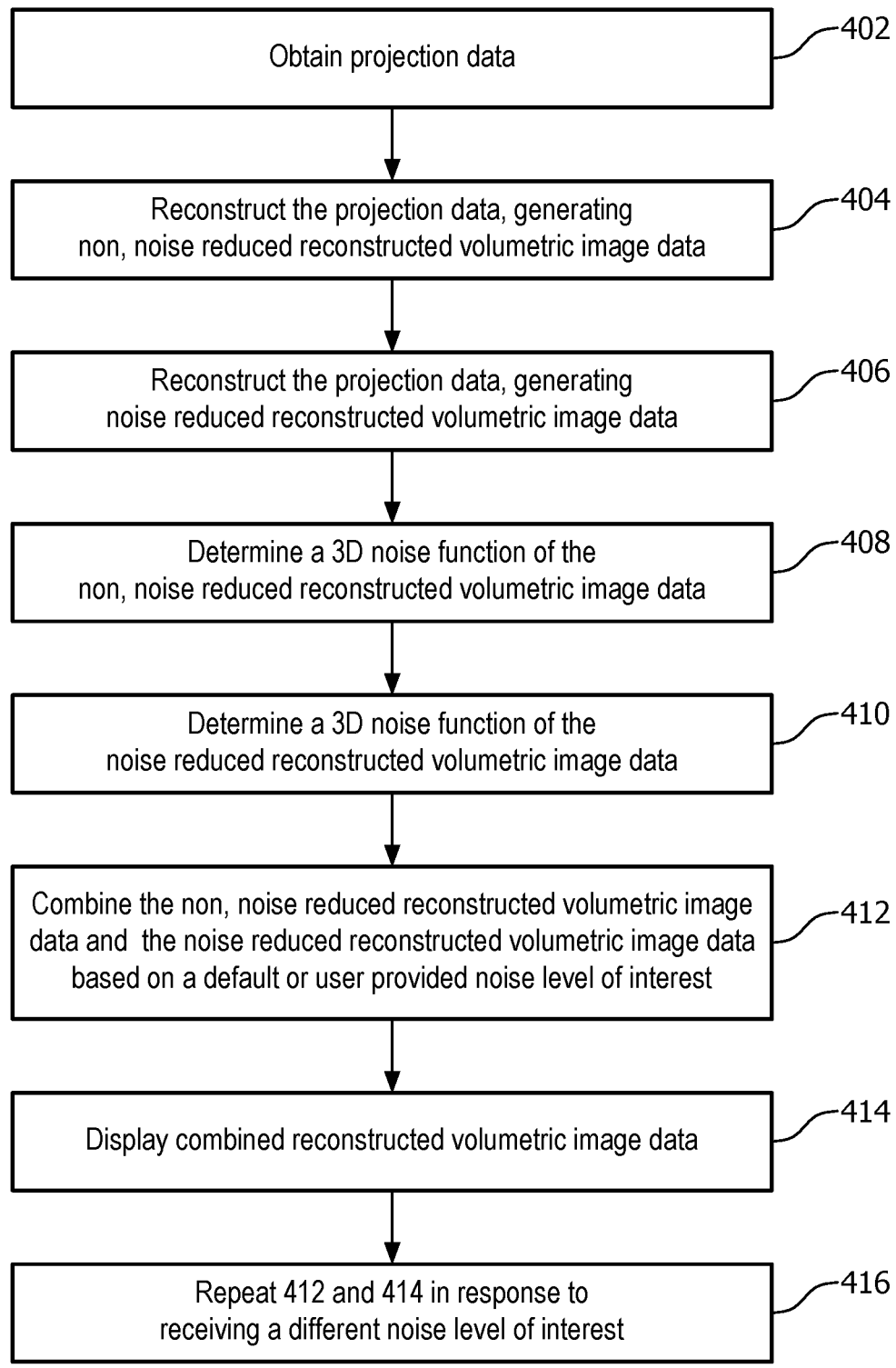
FIG. 4 illustrates an example method for reconstructing the same projection data with two different reconstruction algorithms, one a de-noising reconstruction algorithm, combining the reconstructed image data of both reconstruction algorithms based on a nose level of interest, and displaying the combined reconstructed image data.

FIG. 4 illustrate an example method in which combined non, reduced noise and reduced noise volumetric image data is generated and displayed.

It is to be appreciated that the ordering of the acts in the methods is not limiting. As such, other orderings are contemplated herein. In addition, one or more acts may be omitted and/or one or more additional acts may be included.

At 402, projection data is obtained.

At 404, a reconstructor reconstructs the projection data, generating non, de-noised reconstructed volumetric image data.

At 406, the same or different reconstructor reconstructs the projection data, generating reduced noise (or de-noised) reconstructed volumetric image data.

At 408, a 3D noise function of the reconstructed volumetric image data is determined. At 410, a 3D noise function of the reduced noise reconstructed volumetric image data is determined.

At 412, the non, noise reduced reconstructed volumetric image data and the reduced noise reconstructed volumetric image data are combined based on a default or user provided noise value of interest.

In one instance, the noise value of interest is determined through the ROI overlay and/or viewport of FIG. 3.

At 414, the combined reconstructed volumetric image data is displayed.

At 416, in response to receiving a different noise value of interest, acts 412 and 414 are repeated.

The above acts may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The above can be utilized in connection with a radiologist reading images of a currently scanned subject. Alternatively, the above can be utilized in connection with a radiologist reading images of one or more previously scanned subject. The latter may include accessing a database of previously scanned subjects and allowing the radiologist to view results from different de-noising reconstructions, results from different combinations based on different noise levels.

The latter may also be utilized to visual potential effects of lowering dose for a scan. This may include first determining and/or obtaining a relationship between noise and dose, and then providing either a dose or a noise of interest, displaying the corresponding noise or dose, and processing and presenting the reconstructed volumetric image data. In this case, the user may be able to dynamically change dose and/or noise parameters and visualize the effects through subsequent reconstructions.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   processing projection data with a first reconstruction algorithm and reconstructing first volumetric image data, wherein the first volumetric image data has a first 3D noise function;
   processing the same projection data with a second different reconstruction algorithm and reconstructing second volumetric image data, wherein the second volumetric image data has a second 3D noise function, which is different from the first 3D noise function;
   determining a physical mapping between voxels of the first volumetric image data and voxels of the second volumetric image data;
   visually presenting the first volumetric image data or the second volumetric image data in a main viewport; and
   based on the determined physical mapping, visually presenting:
   a sub-portion of the second volumetric image data in a region of interest overlaid over a corresponding sub-portion of the visually presented first volumetric image data in the main viewport, or
   a sub-portion of the first volumetric image data in the region of interest overlaid over a corresponding sub-portion of the visually presented second volumetric image data in the main viewport.

2. The method of claim 1, wherein the region of interest overlay has a first viewing area, and further comprising:
   visually presenting a pop up viewport with a second viewing area, which is larger than the first viewing area, wherein the pop up viewport visually presents that same sub-portion the other of the first and the second volumetric image data visually presented in the region of interest, but magnified based on a ratio of the second viewing area to the first viewing area.

3. The method of claim 1, wherein the first volumetric image data is non-reduced noise volumetric image data, and the second volumetric image data is reduced noise volumetric image data.

4. The method of claim 1, wherein the first volumetric image data is non-reduced noise volumetric image data, and the second volumetric image data is a combination of the non-reduced noise volumetric image data and reduced noise volumetric image data.

5. The method of claim 1, further comprising:
   receiving a signal indicating a change in position of the region of interest overlay;
   moving the region of interest overlay to the position indicated in the signal; and
   updating the volumetric image data displayed in the region of interest overlay based on the position.

6. The method of claim 1, further comprising
   switching the volumetric image data displayed in the region of interest overlay between the first volumetric image data and the second volumetric image data.

7. The method of claim 1, further comprising
   identifying a noise level of interest based on the volumetric image data displayed in the region of interest overlay.

8. The method of claim 7, further comprising:
   combining the first and second volumetric imaged data, creating combined volumetric image data, based on the identified noise level of interest; and
   visually displaying the combined volumetric image data.

9. The method of claim 1, further comprising:
   receiving a user defined target noise level;
   combining the first and second volumetric imaged data, creating combined volumetric image data based on a blending algorithm and the user defined target noise level; and
   visually displaying the combined volumetric image data.

10. The method of claim 9, further comprising:
    receiving a change in the user defined target noise level;
    re-combining the first and second volumetric imaged data, creating second combined volumetric image data based on the blending algorithms and the changed user defined target noise level; and visually displaying the second combined volumetric image data.

11. A system, comprising:
processor circuitry configured to:
  process projection data with a first reconstruction algorithm and reconstruct first volumetric image data, wherein the first volumetric image data has a first 3D noise function;
  process the same projection data with a second different reconstruction algorithm and reconstruct second volumetric image data, wherein the second volumetric image data has a second 3D noise function, which is different from the first 3D noise function; and
  determine a physical mapping between voxels of the first volumetric image data and voxels of the second volumetric image data; and
a display configured to:
  visually present the first volumetric image data or the second volumetric image data in a main viewport; and
  based on the determined physical mapping, visually present:
    a sub-portion of the second volumetric image data in a region of interest overlaid over a corresponding sub-portion of the visually presented first volumetric image data in the main viewport, or
    a sub-portion of the first volumetric image data in the region of interest overlaid over a corresponding sub-portion of the visually presented second volumetric image data in the main viewport.

12. The system of claim 11, wherein the display is configured to visually display a popup viewport with a magnified view of the sub-portion of a de-noised volumetric image data in the overlay.

13. The system of claim 11, wherein the overlay is moveable, and the processor circuitry is further configured to update the data in the overlay and in a pop up viewport in response to the overlay being moved to a different location over the visually displayed image data.

14. The system of claim 11, wherein the processor circuitry is further configured to receive a noise level of interest as a user input and combine the first and the second volumetric image data based on the received noise level of interest.

15. The system of claim 13, wherein the processor circuitry is further configured to receive a change in a noise level of interest as a subsequent user input and combine the first and the second volumetric image data based on the change in the noise level of interest.

* * * * *